(12) United States Patent
Chen et al.

(10) Patent No.: US 10,499,802 B1
(45) Date of Patent: Dec. 10, 2019

(54) MOUTH-OPENING DEVICE CUSTOM-MADE THROUGH 3-DIMENSIONAL PRINTING

(71) Applicant: Kaohsiung Medical University, Kaohsiung (TW)

(72) Inventors: Chia-Hsin Chen, Kaohsiung (TW); Yi-Hung Pai, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 16/118,897

(22) Filed: Aug. 31, 2018

(51) Int. Cl.
  *A61B 1/24* (2006.01)
  *A61B 34/10* (2016.01)

(52) U.S. Cl.
  CPC ............... *A61B 1/24* (2013.01); *A61B 34/10* (2016.02)

(58) Field of Classification Search
  CPC .. A61B 1/24; A61B 1/32; A61B 1/267; A61B 1/06; A61B 90/14; A61B 90/50; A61B 90/57; A61B 34/10; A61B 2034/102; A61B 2034/104; A61B 2034/105; A61B 2034/107; A61B 2034/108; A61C 17/06; A61C 17/08; A61C 17/02; A61C 17/24; A61C 17/0206
  USPC ...................... 600/223–245; 433/93, 94, 140
  See application file for complete search history.

(56) References Cited

U.S. PATENT DOCUMENTS

| | | | | |
|---|---|---|---|---|
| 4,887,965 A * | 12/1989 | Fox | ........................... | A61B 1/24 433/140 |
| 5,097,820 A * | 3/1992 | Shulman | .................. | A61B 1/24 600/237 |
| 5,347,996 A * | 9/1994 | Huan | ....................... | A61B 1/24 128/859 |
| 5,733,121 A * | 3/1998 | Goode | ............... | A61B 17/0206 433/140 |
| 8,989,567 B1* | 3/2015 | Pulido | .................. | A61C 9/0053 396/16 |
| 2017/0273550 A1* | 9/2017 | Wu | .......................... | A61B 1/32 |

* cited by examiner

*Primary Examiner* — Pedro Philogene
(74) *Attorney, Agent, or Firm* — Jackson IPG PLLC; Demian K. Jackson

(57) ABSTRACT

A device is provided for opening mouth. The device is custom-made through 3-dimensional (3D) printing. The overall framework is printed out after 3D-scanning the oral cavity, which meets a patient's oral shape. The present invention practically and effectively fabricates a custom-made mouth-opening device. The mouth's structure changed after surgery is taken into consideration, so that the patient can easily open the mouth with one hand. Furthermore, because the weight overall is light, the whole single-hand operation feels no heavy. The prolonged work of dental rehabilitation required by the patient is met. The device is easy to be cleaned. The feature of high material strength yet with proper softness is achieved. The comfort of use is increased for the patient with life quality enhanced. The effectiveness of rehabilitation and intervention is improved. The cost of custom-made medical material is effectively reduced.

9 Claims, 4 Drawing Sheets

MOUTH-OPENING DEVICE CUSTOM-MADE THROUGH 3-DIMENSIONAL PRINTING

TECHNICAL FIELD OF THE INVENTION

The present invention relates to a mouth-opening device; more particularly, to easily opening a mouth of a patient through a single-hand operation, where an overall framework of the device is printed out after 3D-scanning (3D: 3-dimensional) oral cavity for meeting individual oral shape.

DESCRIPTION OF THE RELATED ARTS

Medical developments and advances have made the survival of cancer patients increased with life expectancy. Therefore, multifaceted intervention models for maintaining or enhancing the overall function and the life quality of the cancer survivors are the key objectives of cancer rehabilitation. The treatments for oral cancer patients often associate with surgeries, chemotherapies and radiation therapies. Due to the tumor itself or oral soft tissue fibrosis arisen after treatment, trismus may occur to affect oral feeding and cleaning functions. Therefore, problems like malnutrition and infection are more likely appear.

Currently, oral cancer patients are increased in number. Some patients have difficulties in mouth-opening because of oral tumor invasion or IMRT radiation; and some others have problems of insufficient mouth-opening. The interventions for difficulties in mouth-opening are mainly oral rehabilitation trainings with the coordination of proper intraoral orthoses for progressive stretching exercises. Current mouth-opening orthoses with their disadvantages are as follows:

1. Wooden spatulas are commonly used by patients. The continuously increased number of spatulas stacked are used to increase the opening width of the mouth. Although these devices are relatively simple on using, but they all have a certain degree of risk. For example, a wood material with more hardness may easily damage oral tissues. If the force used is too big, it may lead to breakage of the spatulas and further stabs oral tissues, which is very dangerous.

2. Mouth-pressure devices can be used. However, their high prices and very large volumes affect the wishes of use by the patients.

3. Steel-plate-molded devices are provided. But patients may feel very painful at the time of use. It may often result in the patients' resistance or escape from therapy due to unbearable pain during rehabilitation. Thereby, the effectiveness of rehabilitation may be reduced.

Currently, there is no 3D printing technology of making a mouth-opening device according to personal requirements of rehabilitation with the above disadvantages conquered. Hence, the prior arts do not fulfill all users' requests on actual use.

SUMMARY OF THE INVENTION

The main purpose of the present invention is to practically and effectively make a preferable custom-made mouth-opening device through 3D printing, where the structural changes of oral cavity of a patient formed after surgery is taken into consideration, so that the device can be used with one hand for operation; through a screw pivotally connected, a first supporting body is movable and operated in multiple angles for leaning on a second supporting body in a space; after the first and second supporting bodies are put in the oral cavity in a closed state, a nut screwed on the screw is rotated to prop the first supporting body against the second supporting body used as a fixed end; consequently, the patient's mouth can be easily opened with one hand; furthermore, because the weight overall is light, the whole single-hand operation is done without feeling heavy; the prolonged work of dental rehabilitation required by the patient is met; at the same time, the device is easy to be cleaned; and the feature of high material strength yet with proper softness is achieved.

Another purpose of the present invention is to create a device with a series of related 3D modeling, where, through 3D scanning the oral cavity, a 3D drawing is created; the drawing is processed through 3D-graphics design and 3D-printing for making biomedical materials; the entire process can be custom-made according to the requirements of the patient, so that the mouth-opening device is more appropriate for the patient's rehabilitation; the comfort of use is increased for the patient with life quality enhanced; the effectiveness of rehabilitating intervention is improved to accelerate the patient's recovery; not only the lifestyle is functioned better, but also the most effective medical treatment is achieved; the cost of the custom-made medical material is effectively reduced; and the device is not only used by oral cancer patients, but also greatly relieves users from difficulties on mouth-opening or -closing.

To achieve the above purposes, the present invention is a custom-made device fabricated through 3D printing for opening mouth, comprising a first supporting body, a second supporting body and a screw, where the first supporting body comprises a first body, a first pivoting part and a first supporting part; the first body has a first space; the first pivoting part extends out from a first end of the first body; the first supporting part extends out from a second end of the first body; the first supporting body is deposed in the oral cavity; the second supporting body comprises a second body, a second pivoting part and a second supporting part; the second body has a second space; the second pivoting part extends out from a first end of the second body; the second supporting part extends out from a second end of the second body; the second supporting body is deposed in the oral cavity; the first and the second supporting bodies pivot with each other through the first and the second pivoting parts; the first supporting part is coordinated with the second supporting part to open and close the oral cavity; the screw has a third end pivoted in the first space of the first supporting body; the screw has a fourth end movable and operated at a various of angles to lean on in the second space of the second supporting body; the screw is screwed with a nut; an overall framework of the device is printed out through 3D-printing after 3D-scanning an oral cavity to meet the shape of the oral cavity; and, after the first and the second supporting bodies are in a closed state to be deposed into the oral cavity, a single hand rotates the nut screwed on the screw to open the oral cavity by propping the first supporting body against the second supporting body as a fixed end with the coordination of the second space which is bigger than the first space.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
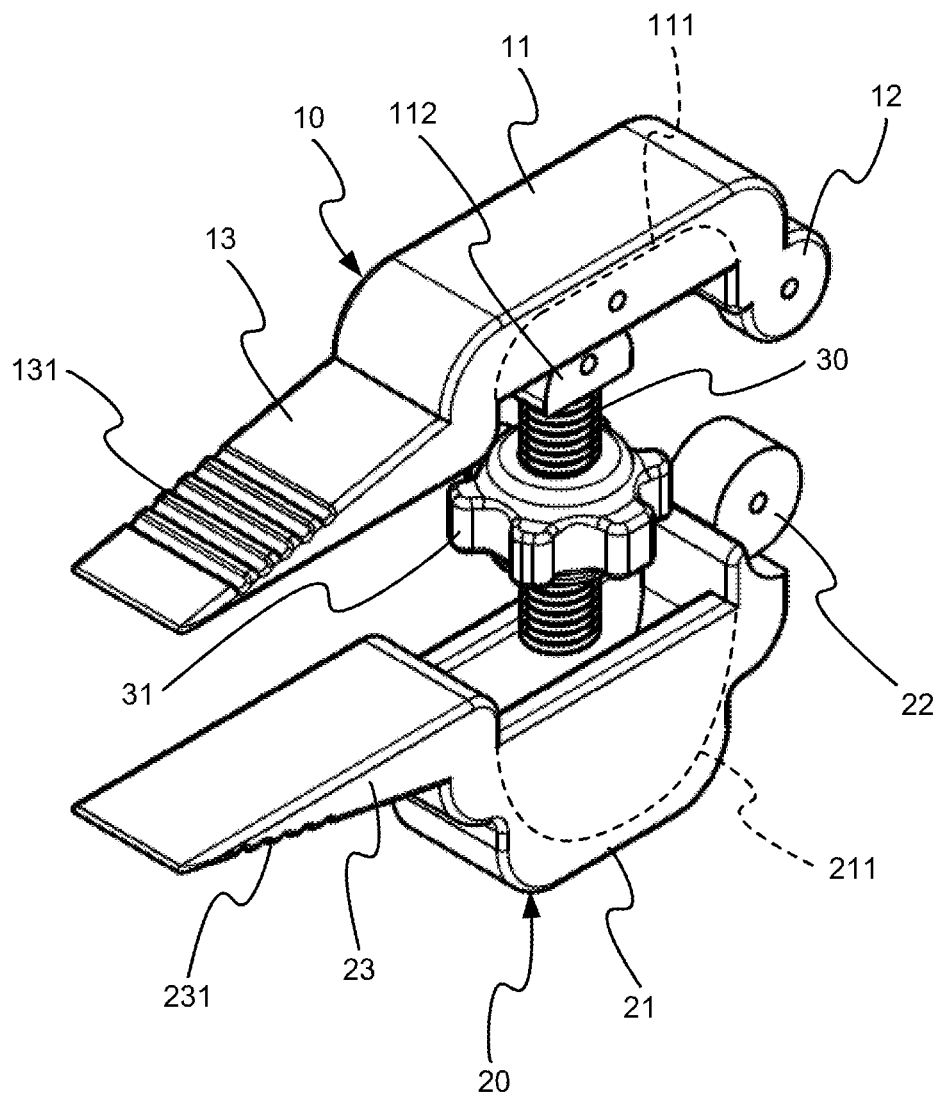
FIG. 1 is the view showing the exploded first state-of-use of the preferred embodiment according to the present invention.
Figure 2:
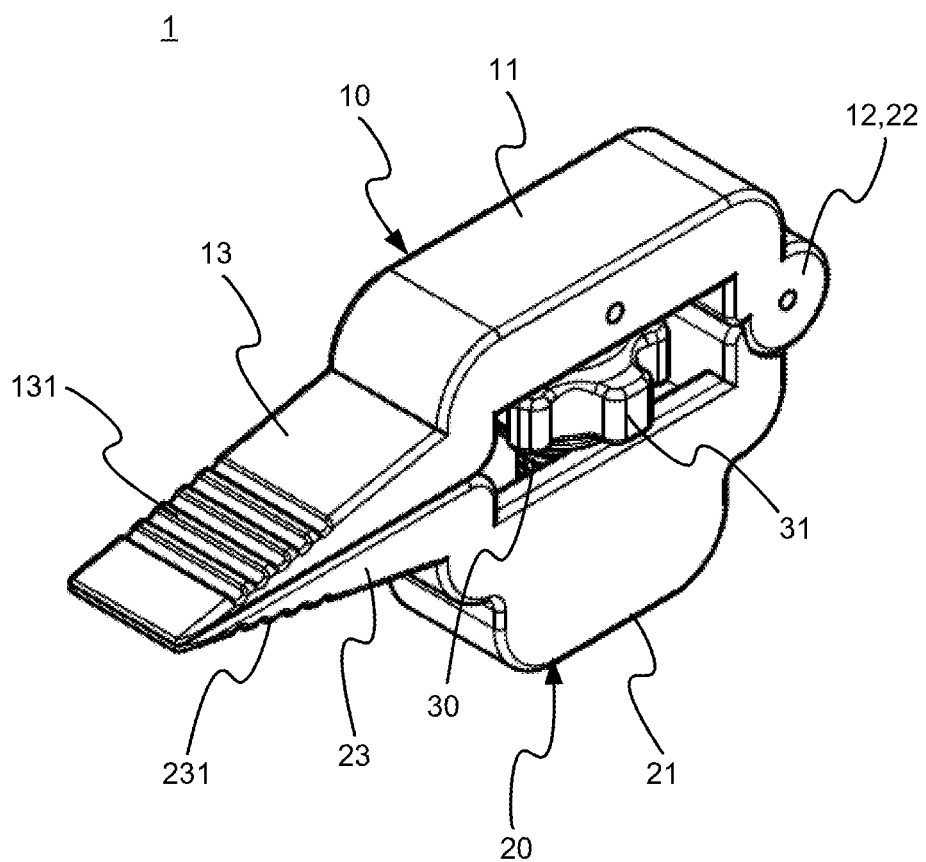
FIG. 2 is the view showing the assembled first state-of-use.

Please refer to FIG. 1 and FIG. 2, which are views showing exploded and assembled first states-of-use of a preferred embodiment according to the present invention. As shown in the figures, the present invention is a custom-made device fabricated through 3-dimensional (3D) printing for opening mouth, where an overall framework is printed out through 3D-printing after 3D-scanning an oral cavity for meeting the shape of the oral cavity. The custom-made device 1 comprises a first supporting body 10, a second supporting body 20 and a screw 30.

The first supporting body 10 comprises a first body 11, a first pivoting part 12 and a first supporting part 13. The first body 11 has a first space 111. The first pivoting part 12 extends out from a first end of the first body 11. The first supporting part 13 extends out from a second end of the first body 11. The first supporting body 10 is deposed in the oral cavity. Therein, the first supporting part 13 has a first occluding surface 131 occupying a part of area of an outer surface of the first supporting part 13; and the first occluding surface 131 is a wavy surface or a grooved surface, but not limited. Because the first support portion 13 has a reinforcing effect for external friction, stability of tight closing is enhanced at supporting point. Hence, any similar structure having such effect belongs to the technical concept of the present invention and can be easily figured out.

The second supporting body 20 comprises a second body 21, a second pivoting part 22 and a second supporting part 23. The second body 21 has a second space 211. The second pivoting part 22 extends out from a first end of the second body 21. The first and the second supporting bodies 10,20 pivot with each other through the first and the second pivoting parts 12,22. The second supporting part 23 extends out from a second end of the second body 21. The second supporting body 20 is deposed in the oral cavity; The second supporting part 23 is coordinated with the first supporting part 13 to open and close the oral cavity. Therein, the first and the second supporting parts 13,23 are in a state of mirroring to each other; the second supporting part 23 has a second occluding surface 231 occupying a part of area of an outer surface of the second supporting part 23; and the second occluding surface 231 is a wavy surface or a grooved surface, but not limited. Because the second support portion 23 has a reinforcing effect for external friction, stability of tight closing is enhanced at supporting point. Hence, any similar structure having such effect belongs to the technical concept of the present invention and can be easily figured out.

The screw 30 has a third end pivoted in the first space 111 of the first supporting body 10; and a fourth end movable and operated at a various of angles to lean on in the second space 211 of the second supporting body 20. The screw 30 is screwed with a nut 31. Therein, a seat 112 is deposed in the first space 112 of the first body 11; and an end of the screw 30 is put in a sink hole (not shown in the figures) formed in the seat 112 to pivot the screw 30 in the first space 111 of the first supporting body 10 through the seat 112.

Thus, a novel custom-made device fabricated through 3D printing for opening mouth is obtained.

The first state-of-use has the following structural features: the first and the second supporting parts 13,23 are progressively flattened from the second ends of the first and the second bodies 11,21 to form long-strip supporting parts; the first and the second supporting bodies 10,20 pivot with each other through the first and the second pivoting parts 12,22 at their rear ends; and the second space 211 of the second supporting body 20 is bigger than the first space 111 of the first supporting body 10. Thus, the first and the second supporting bodies 10,20 can be opened and closed at any degree (°) within 180°; and, with the second supporting body 20 as a fixed end, the first supporting body 30 moves up and down by rotating the nut 30 to obtain a proper opening or closing state as required. On practically using the present invention in a patient's oral cavity, the custom-made device 1 is in a closing state at first to put the first and the second supporting parts 13,23 into the oral cavity. The upper and lower rows of teeth of the patient are bitten on the first and the second occluding surfaces 131,231 of the first and the second supporting parts 13,23. Through the first and second occluding surfaces 131,231 partial wavy or grooved, the frictional force is strengthened for the patient on occluding. At the moment, the patient can rotate the nut 31 screwed on the screw 30 with one hand to further rotate the screw according to rehabilitation needs. Thus, a relative displacement to the screw 30 is obtained by screwing the nuts 31. With the second supporting body 20 as a fixed end, the first supporting body 10 is propped up. Hence, the patient's mouth can be easily opened with one hand for rehabilitation.

Figure 3:
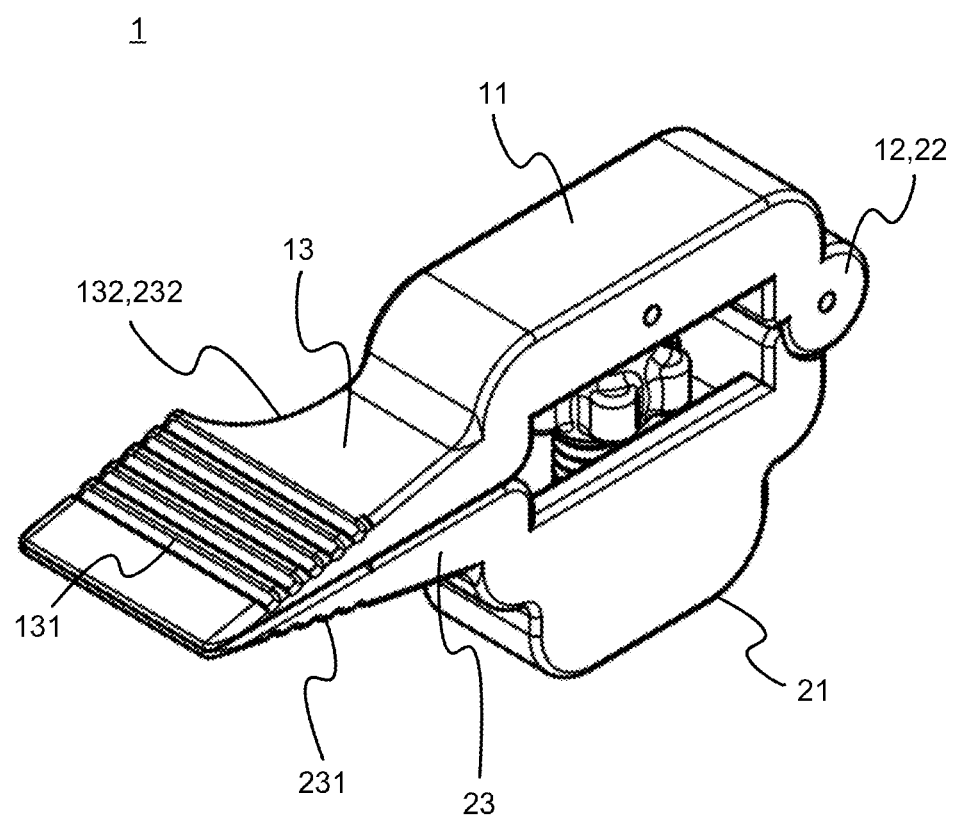
FIG. 3 is the view showing the second state-of-use.
Figure 4:
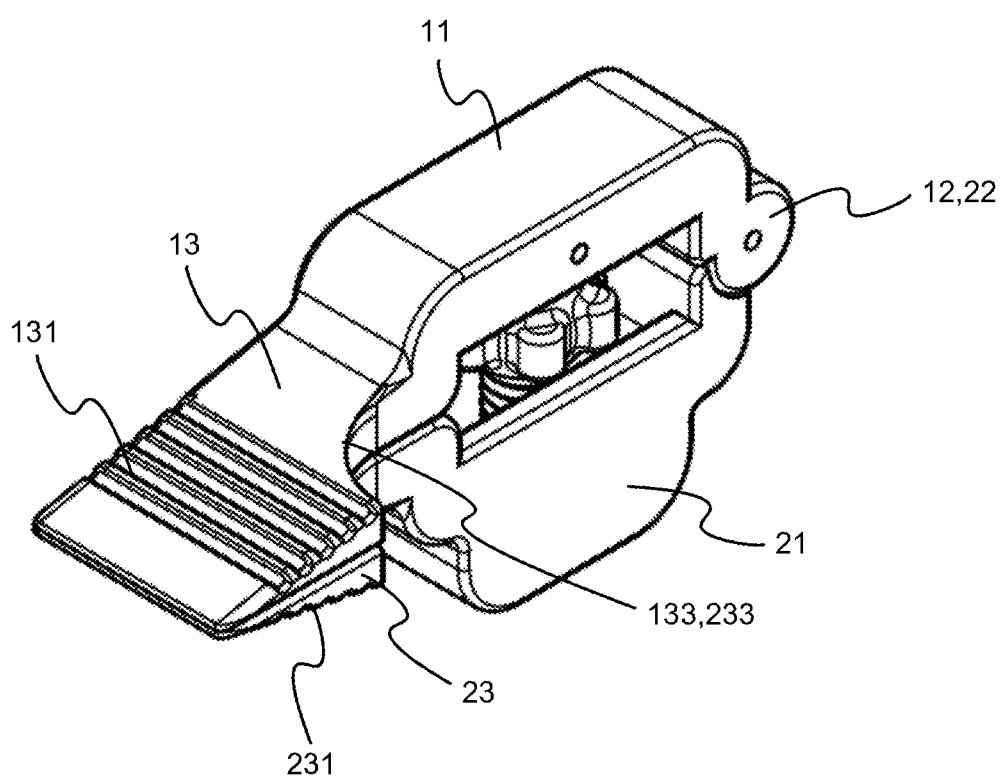
FIG. 4 is the view showing the third state-of-use.

Please refer to FIG. 3 and FIG. 4, which are views showing a second and a third states-of-use. As shown in the figures, a second and a third states-of-use are available. They are different for considering the structural changes of oral cavity after surgery for a patient. In these states-of-use, a first and a second supporting parts 13,23 are progressively flattened and widened from second ends of a first and a second bodies 11,21 to form arc-like supporting parts, respectively. Therein, each front end of the first and the second supporting parts 13,23 bends outwardly at a side to form an arc edge for supporting and occluding at the side. In FIG. 3, the first and the second supporting parts 13,23 bend outwardly at left sides to form a first and a second left arc edges 132,232. In FIG. 4, the first and the second supporting parts 13,23 bend outwardly at right sides to form a first and a second right arc edges 133,233.

The present invention uses a popular 3D-printing manufacture technology to accelerate the developments of custom-made medical materials and devices. Through 3D printing combined with biomedical materials, past custom-made medical materials obtain new values, which are no longer high-priced medical materials. Since the use of oral articulator is an important assistant device or a medical material of correction and protection for related oral health, the present invention creates a device using a series of related 3D modeling with the unique design for personal oral cavity. Through 3D scanning the oral cavity, a 3D drawing is created; and, then, the drawing is processed through 3D-graphics design and 3D-printing for making biomedical materials. The entire process can be custom-made according to the requirements of a patient, so that the mouth-opening device is more appropriate for the patient's rehabilitation. The recovery of the patient can be effectively accelerated. The lifestyle can be functioned better. The most effective medical treatment is achieved.

The present invention practically and effectively makes a preferable custom-made mouth-opening device through 3D printing. The structural changes of oral cavity of a patient formed after surgery is taken into consideration, so that the device can be used with one hand for operation. Through a screw pivotally connected, a first supporting body is movable and operated in multiple angles for leaning on a second supporting body in a space. After the first and second supporting bodies are put in the oral cavity in a closed state, the patient uses a single hand to rotate a nut screwed on the screw to open the oral cavity by propping the first supporting body against the second supporting body as a fixed end with the coordination of the second space which is bigger than the first space. Because the weight overall is light, the whole single-hand operation is done without feeling heavy. The prolonged work of dental rehabilitation required by the patient is met. At the same time, the device is easy to be cleaned. The feature of high material strength yet with proper softness is achieved. The comfort of use by patient is increased with life quality enhanced. The effectiveness of rehabilitating intervention is improved. The cost of custom-made medical material is effectively reduced.

To sum up, the present invention is a custom-made device fabricated through 3D printing for opening mouth, where a custom-made device is fabricated with the consideration of the structural change of oral cavity of a patient formed after surgery for custom-making according to the requirements of the patient; the device is more appropriate for the patient's rehabilitation; the comfort of use is increased for the patient with life quality enhanced; the effectiveness of rehabilitating intervention is improved to accelerate the patient's recovery; the lifestyle is functioned better; the most effective medical treatment is achieved; the cost of custom-made medical material is effectively reduced; and the device is not only used by oral cancer patients, but also greatly relieves users from difficulties on mouth-opening or -closing.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A custom-made device fabricated through 3-dimensional (3D) printing for opening mouth, comprising
   a first supporting body, comprising a first body, a first pivoting part and a first supporting part,
      wherein said first body has a first space; said first pivoting part extends out from a first end of said first body; said first supporting part extends out from a second end of said first body; and said first supporting body is deposed in said oral cavity;
   a second supporting body, comprising a second body, a second pivoting part and a second supporting part,
      wherein said second body has a second space; said second pivoting part extends out from a first end of said second body; said second supporting part extends out from a second end of said second body; and said second supporting body is deposed in said oral cavity;
      wherein said first and said second supporting bodies pivot with each other through said first and said second pivoting parts; and
      wherein said first supporting part is coordinated with said second supporting part to open and close said oral cavity; and
   a screw,
      wherein said screw has a third end pivoted in said first space of said first supporting body; said screw has a fourth end movable and operated at a various of angles to lean on in said second space of said second supporting body; and said screw is screwed with a nut,
      wherein an overall framework is printed out through 3D-printing after 3D-scanning an oral cavity to meet the shape of said oral cavity; and
      wherein, after said first and said second supporting bodies are in a closed state to be deposed into said oral cavity, a single hand rotates said nut screwed on said screw to open said oral cavity by propping said first supporting body against said second supporting body as a fixed end with the coordination of said second space which is bigger than said first space.

2. The custom-made device according to claim 1, wherein said first and said second supporting parts are in a state of mirroring to each other.

3. The custom-made device according to claim 1, wherein each one of said first and said second supporting parts has an occluding surface occupying a part of area of an outer surface of said each one.

4. The custom-made device according to claim 3, wherein said occluding surface is a surface selected from a group consisting of a wavy surface and a grooved surface.

5. The custom-made device according to claim 1, wherein said first and said second supporting parts are progressively flattened from said second ends of said first and said second bodies to obtain long-strip supporting parts, respectively.

6. The custom-made device according to claim 1, wherein said first and said second supporting parts are progressively flattened and widened from said second ends of said first and said second bodies to obtain arc-like supporting parts, respectively.

7. The custom-made device according to claim 6, wherein each one of front ends of said first and said second supporting parts separately bends at a side outwardly from said oral cavity to obtain a curved arc to support and occlude at said side.

8. The custom-made device according to claim 1, wherein a seat is deposed in said first space of said first body; and an end of said screw is deposed in a sink hole obtained in said seat to pivot said screw in said first space of said first supporting body through said seat.

9. The custom-made device according to claim 1, wherein, with said second supporting body as a fixed end, said first supporting body moves up and down by rotating said nut to obtain a state selected from a group consisting of an opening state and a closing state.

* * * * *